(12) United States Patent
Bufalini et al.

(10) Patent No.: US 8,700,210 B2
(45) Date of Patent: Apr. 15, 2014

(54) SYSTEMS, METHODS AND COMPUTER PROGRAM PRODUCTS FOR VISUALLY EMPHASIZING PORTIONS OF A MEDICATION STORAGE DEVICE

(75) Inventors: Brian A. Bufalini, Aliquippa, PA (US); Fabian R. Reza, Pittsburgh, PA (US); Mark W. Leng, Venetia, PA (US)

(73) Assignee: Aesynt Incorporated, Cranberry, PA (US)

( * ) Notice: Subject to any disclaimer, the term of this patent is extended or adjusted under 35 U.S.C. 154(b) by 253 days.

(21) Appl. No.: 13/248,971

(22) Filed: Sep. 29, 2011

(65) Prior Publication Data
US 2013/0082581 A1    Apr. 4, 2013

(51) Int. Cl.
*G06F 17/00*    (2006.01)

(52) U.S. Cl.
USPC .......................................... 700/242; 700/243

(58) Field of Classification Search
USPC .................. 700/242, 240, 241, 243
See application file for complete search history.

(56) References Cited

U.S. PATENT DOCUMENTS

| | | |
|---|---|---|
| 4,717,042 A | 1/1988 | McLaughlin |
| 4,785,969 A | 11/1988 | McLaughlin |
| 4,847,764 A | 7/1989 | Halvorson |
| 5,014,875 A | 5/1991 | McLaughlin et al. |
| 5,190,185 A | 3/1993 | Blechl |
| 5,292,029 A | 3/1994 | Pearson |
| 5,314,243 A | 5/1994 | McDonald et al. |
| 5,346,297 A | 9/1994 | Colson, Jr. et al. |
| 5,377,864 A | 1/1995 | Blechl et al. |
| 5,405,048 A | 4/1995 | Rogers et al. |
| 5,408,443 A | 4/1995 | Weinberger |
| 5,431,299 A | 7/1995 | Brewer et al. |
| 5,460,294 A | 10/1995 | Williams |
| 5,468,110 A | 11/1995 | McDonald et al. |
| 5,480,062 A | 1/1996 | Rogers et al. |
| 5,520,450 A | 5/1996 | Colson, Jr. et al. |
| 5,564,803 A | 10/1996 | McDonald et al. |
| 5,593,267 A | 1/1997 | McDonald et al. |
| 5,661,978 A | 9/1997 | Holmes et al. |
| D384,578 S | 10/1997 | Wangu et al. |
| 5,713,485 A | 2/1998 | Liff et al. |
| 5,716,114 A | 2/1998 | Holmes et al. |
| 5,745,366 A | 4/1998 | Higham et al. |
| 5,761,877 A | 6/1998 | Quandt |
| 5,797,515 A | 8/1998 | Liff et al. |
| 5,805,456 A | 9/1998 | Higham et al. |
| 5,842,976 A | 12/1998 | Williamson |
| 5,878,885 A | 3/1999 | Wangu et al. |
| 5,880,443 A | 3/1999 | McDonald et al. |
| 5,883,806 A | 3/1999 | Meador et al. |

(Continued)

OTHER PUBLICATIONS

U.S. Appl. No. 13/076,762, filed Mar. 31, 2011, titled "Storage Devices, Systems, and Methods for Facilitating Medication Dispensing and Restocking".

(Continued)

*Primary Examiner* — Timothy Waggoner
(74) *Attorney, Agent, or Firm* — Alston & Bird LLP

(57) ABSTRACT

Methods, apparatuses and computer program products are provided for facilitating the expedited dispensing of medications from an automated medication storage device. In this regard, a method may cooperate with the medication storage device to facilitate the presentation of one or more highlighting lights and projection displays that include features to expedite the removal, stocking and counting of medications safely and effectively.

24 Claims, 7 Drawing Sheets

(56) References Cited

U.S. PATENT DOCUMENTS

| | | | |
|---|---|---|---|
| 5,893,697 A | 4/1999 | Zini et al. |
| 5,905,653 A | 5/1999 | Higham et al. |
| 5,912,818 A | 6/1999 | McGrady et al. |
| 5,927,540 A | 7/1999 | Godlewski |
| 5,940,306 A | 8/1999 | Gardner et al. |
| 5,971,593 A | 10/1999 | McGrady |
| 6,003,006 A | 12/1999 | Colella et al. |
| 6,011,999 A | 1/2000 | Holmes |
| 6,021,392 A | 2/2000 | Lester et al. |
| 6,039,467 A | 3/2000 | Holmes |
| 6,065,819 A | 5/2000 | Holmes et al. |
| 6,068,156 A | 5/2000 | Liff et al. |
| 6,109,774 A | 8/2000 | Holmes et al. |
| 6,112,502 A | 9/2000 | Frederick et al. |
| 6,116,461 A | 9/2000 | Broadfield et al. |
| 6,151,536 A | 11/2000 | Arnold et al. |
| 6,170,230 B1 | 1/2001 | Chudy et al. |
| 6,176,392 B1 | 1/2001 | William et al. |
| 6,189,727 B1 | 2/2001 | Shoenfeld |
| 6,223,934 B1 | 5/2001 | Shoenfeld |
| 6,256,967 B1 | 7/2001 | Hebron et al. |
| 6,283,322 B1 | 9/2001 | Liff et al. |
| 6,289,656 B1 | 9/2001 | Wangu et al. |
| 6,338,007 B1 | 1/2002 | Broadfield et al. |
| 6,339,732 B1 | 1/2002 | Phoon et al. |
| 6,361,263 B1 | 3/2002 | Dewey et al. |
| 6,370,841 B1 | 4/2002 | Chudy et al. |
| 6,449,927 B2 | 9/2002 | Hebron et al. |
| 6,471,089 B2 | 10/2002 | Liff et al. |
| 6,497,342 B2 | 12/2002 | Zhang et al. |
| 6,499,270 B2 | 12/2002 | Peroni et al. |
| 6,532,399 B2 | 3/2003 | Mase |
| 6,564,121 B1 | 5/2003 | Wallace et al. |
| 6,581,798 B2 | 6/2003 | Liff et al. |
| 6,609,047 B1 | 8/2003 | Lipps |
| 6,611,733 B1 | 8/2003 | De La Huerga |
| 6,625,952 B1 | 9/2003 | Chudy et al. |
| 6,640,159 B2 | 10/2003 | Holmes et al. |
| 6,650,964 B2 | 11/2003 | Spano, Jr. et al. |
| 6,671,579 B2 | 12/2003 | Spano, Jr. et al. |
| 6,681,149 B2 | 1/2004 | William et al. |
| 6,742,671 B2 | 6/2004 | Hebron et al. |
| 6,755,931 B2 | 6/2004 | Vollm et al. |
| 6,760,643 B2 | 7/2004 | Lipps |
| 6,776,304 B2 | 8/2004 | Liff et al. |
| 6,785,589 B2 | 8/2004 | Eggenberger et al. |
| 6,790,198 B1 | 9/2004 | White et al. |
| 6,814,254 B2 | 11/2004 | Liff et al. |
| 6,814,255 B2 | 11/2004 | Liff et al. |
| 6,847,861 B2 | 1/2005 | Lunak et al. |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 | 5/2006 | Broadfield et al. |
| 7,052,097 B2 | 5/2006 | Meek, Jr. et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,171,277 B2 | 1/2007 | Engleson et al. |
| 7,203,571 B2 | 4/2007 | Kirsch et al. |
| 7,218,231 B2 | 5/2007 | Higham |
| 7,228,198 B2 | 6/2007 | Vollm et al. |
| 7,249,688 B2 | 7/2007 | Hunter et al. |
| 7,268,780 B2 * | 9/2007 | Shibano ..................... 700/17 |
| 7,348,884 B2 | 3/2008 | Higham |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,554,449 B2 | 6/2009 | Higham |
| 7,571,024 B2 | 8/2009 | Duncan et al. |
| 7,588,167 B2 | 9/2009 | Hunter et al. |
| 8,082,061 B2 * | 12/2011 | Segal et al. ............... 700/232 |
| 8,446,288 B2 * | 5/2013 | Mizushima et al. ......... 700/245 |
| 2009/0014461 A1 * | 1/2009 | Omura et al. ............... 221/156 |

OTHER PUBLICATIONS

U.S. Appl. No. 13/235,178, filed Sep. 16, 2011, titled "Systems, Methods and Computer Program Product for Monitoring Interactions With a Medication Storage Device."

* cited by examiner

SYSTEMS, METHODS AND COMPUTER PROGRAM PRODUCTS FOR VISUALLY EMPHASIZING PORTIONS OF A MEDICATION STORAGE DEVICE

TECHNOLOGICAL FIELD

Embodiments of the present invention relate generally to medication storage devices and associated methods and, more particularly, using lighting to aid a user when interacting with the medication storage devices.

BACKGROUND

Medication dispensing cabinets have been developed to store and controllably dispense a variety of medications. A medication dispensing cabinet may include a cabinet body with one or more drawers that are slideably disposed within the cabinet body. The drawers store the various medications. While some of the drawers may be unlatched and freely openable, other drawers may be locked in order to more closely control access to the medications stored in the locked drawers.

Some medication dispensing cabinets are automated and, as such, include or are otherwise associated with a computer that controls access to the compartments that store medications within the cabinet. The computer may be configured to allow access to only authorized users, such as pharmacists who stock the cabinet and medical providers who remove medications from the cabinet.

The amount of time it takes for the medical provider to interact with the computer and access the respective drawer can vary based on the type of medication dispensing cabinets and their computer control systems. While medication storage cabinets are important tools in loss prevention of narcotics as well as in providing the proper medication to each patient, any time spent interacting with the medication storage cabinets is time that the medical providers cannot be with their patients.

Accordingly, there is a need in the art for an improved system and method for dispensing medication that allows healthcare professionals to dispense medication for the patients under their care in a more rapid, efficient, and accurate manner.

BRIEF SUMMARY

Methods, apparatuses and computer program products are provided according to embodiments of the present invention for using light projectors and/or other devices to aid a user when interacting with the medication storage devices. For example, a light projector can comprise a light source configured to: project light to illuminate a first medication storage compartment of a medication storage device without illuminating a second medication storage compartment of the medication storage device. Likewise, the projector's light source can be configured to project the light to illuminate the second medication storage compartment of the medication storage device without illuminating the first medication storage compartment of the medication storage device.

The light projector can further comprise at least one reflective surface that is configured to direct light projected onto the medication storage device. The at least one reflective surface can be configured to be moved to cause either the first medication storage compartment to be illuminated or the second medication storage compartment to be illuminated.

The light projector can be included in the medication storage device and/or located remote or otherwise separate from the medication storage device (e.g., in a room's ceiling or wall and/or mounted on a stand located proximate to the medication storage device). When separate from the medication storage device, the projector can include circuitry that is configured to communicate with the circuitry included in the storage device.

The medication storage device can comprise a drawer that includes the first and/or second medication storage compartments. The medication storage compartments can be lidded and/or un-lidded pockets that may or may not be located adjacent to each other in the drawer.

The light projector can be configured to project light that highlights at least one storage compartment included in the medication storage device and moves as an indicator for the next stage as the user progresses through the workflow. In some embodiments, the light projector can be configured to project user-readable information on at least one storage compartment included in the medication storage device.

Likewise, one or more methods and computer readable media can be implemented that include, among other things, projecting light onto a medication storage device, comprising: projecting light, using a light projector, to illuminate a first medication storage compartment of the medication storage device, wherein illuminating the first medication storage compartment occurs without illuminating a second medication storage compartment of the medication storage device; and projecting the light, using the light projector, to illuminate the second medication storage compartment of the medication storage device, wherein illuminating the second medication storage compartment occurs without illuminating the first medication storage compartment of the medication storage device.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
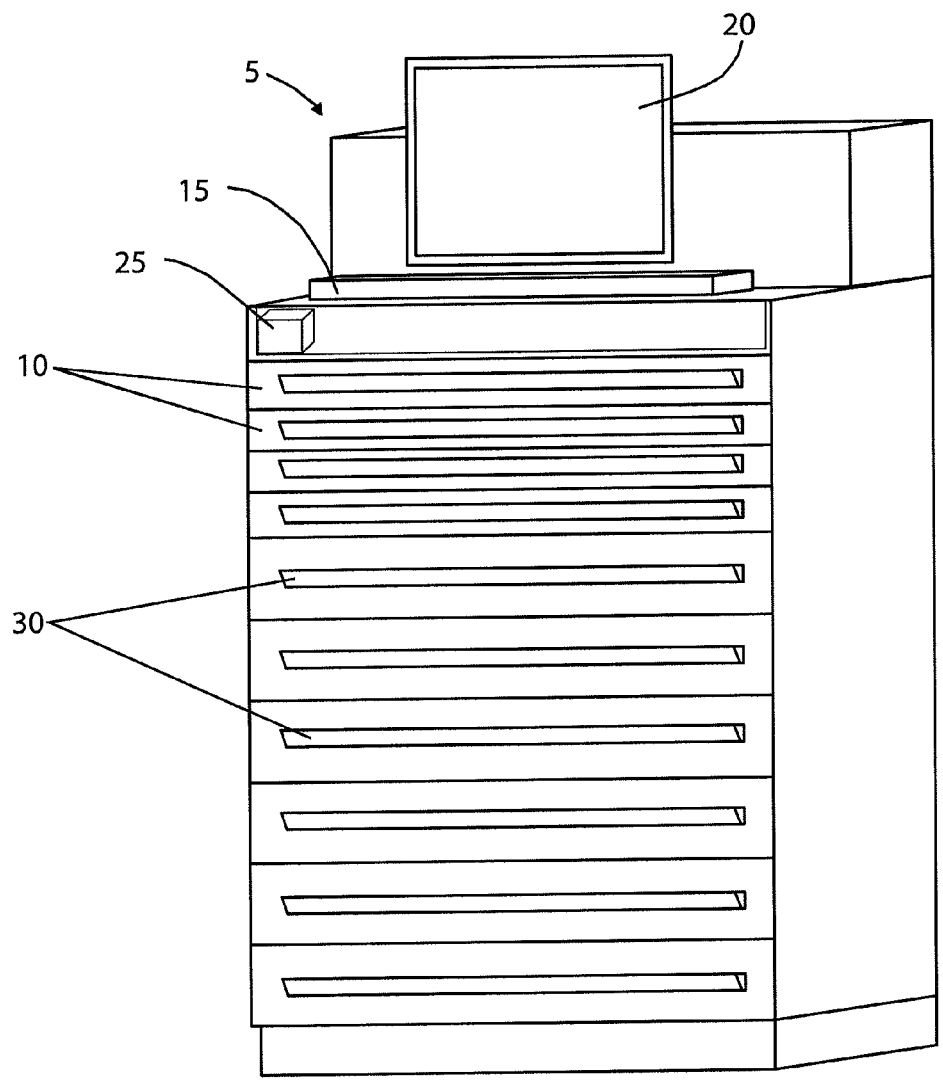
FIG. 1 illustrates an automated storage device in accordance with some example embodiments discussed herein.

Embodiments of the present inventions now will be described more fully hereinafter with reference to the accompanying drawings, in which some, but not all embodiments of the inventions are shown. Indeed, embodiments of these inventions may be embodied in many different forms and should not be construed as limited to the embodiments set forth herein; rather, these embodiments are provided so that this disclosure will satisfy applicable legal requirements. Like reference numerals refer to like elements throughout.

The storage devices, systems, and methods of embodiments of the present invention may be used by healthcare facilities, such as hospitals, physicians' offices, healthcare clinics, and any other facility that manages and/or stores drugs and/or other materials for patient use. The storage devices, systems, and methods described herein can be configured to, for example, (1) indicate which pocket the user needs to access by highlighting the pocket with a directing light, (2) minimize the number of times the user has to look down and up from a storage device's monitor to a drawer and vice-versa, (3) improve the speed of the workflow (e.g., the user's interactions with the storage device), and (4) reduce the likelihood of a user taking the wrong medication from the storage device, among other things. Further, although nurses are one example of a type of user (as they are often tasked with removing medication stored in an automated storage device) and examples with a nurse are sometimes used in the description that follows, it is understood that the described embodiments apply to any type of user who may interact with an automated storage device, including pharmacists, nurses, nurse technicians, pharmacy technicians, physicians, laboratory personnel, respiratory therapists, and others. Furthermore, although the examples of a user interfacing with an automated storage device for the purposes of removing medications are predominantly described below, one skilled in the art in light of this disclosure would recognize that the embodiments are also applicable to users interfacing with the automated storage device for the purpose of taking inventory, conducting counts of medications in the storage device (including, e.g., pocket-specific "blind counts"), stocking the storage device, and performing other tasks that may require access to the medication storage compartments in the automated storage device. In addition, the phrase "storage device" is intended to include any type of automated storage device, including automated dispensing cabinet (ADC), unit-based cabinet (UBC), automated dispensing device (ADD), automated distribution cabinet, medication dispensing cabinet, automated dispensing machine (ADM), and/or any other type of automated medication storage and retrieval system, including those used in pharmacies, hospitals, and/or elsewhere.

Turning now to FIG. 1, a storage device 5 is shown. For example, some embodiments of the storage device 5 can be similar to and/or include components that are currently included in the cabinets and/or other medication management systems sold and marketed as McKesson's AcuDose-Rx® cabinet, MedCarousel® system and/or Anesthesia-Rx™ cart. The storage device 5 may be configured to store a number of different types and quantities of medications. In this regard, the storage device 5 may include (e.g., define) a plurality of drawers 10, examples of which are discussed below. In addition, access to the drawers 10 may be restricted to certain authorized users and may further be accessible only when medication stored in the particular drawer is to be removed, stocked and/or counted, as described in greater detail below. For example, each drawer 10 may be in a locked state until an authorized user interfaces with the storage device 5 to select for removing a particular medication stored within a particular drawer, at which point the storage device may unlock and/or open the drawer containing the selected medication to allow the user's access. Additionally, one or more drawers may include and/or otherwise function as a display screen onto which a projected display is presented to a user, as described in greater detail below.

The drawers 10 may hold more than just medications, in some cases. For example, certain medical accessories or supplies may also be stored in the automated storage device 5, such as applicators, syringes, keys, prescription pads, cameras, etc., which may also be dispensed, stocked, and/or otherwise handled by the user during an interaction with the storage device 5. Accordingly, although the examples provided below refer to the removal of medications, the dispensing, stocking, transport, counting and/or other type of handling of any item stored in the storage device 5, such as medical accessories, is contemplated herein.

In some embodiments, the storage device 5 can further include various data and/or user input devices, such as input device 15. A data input device may be, for example, a device that receives data from another machine, such as communications modules discussed below, and user input devices may include devices configured to receive inputs from the user, such as touch displays, keyboards, cameras, touchpads, and computer mice, among other things. User input device 15 and display device 20 are shown in FIG. 1, wherein user input device 15 is shown as a keyboard and display device 20 is shown as a touch-sensitive display device.

The user and data input devices can be used to facilitate, among other things, removal transactions. In this regard, the phrase "removal transaction" is used herein to describe the interfacing between the user and the storage device to remove one or more medications to be administered to a single patient. Thus, each removal transaction is associated with a particular selected patient. Furthermore, each user may have multiple removal transactions with the storage device in a single interaction with the storage device (i.e., he or she may remove medications for multiple patients during a single interaction with the storage device). In this regard, the window between the time a user logs into the system (e.g., provides identification credentials indicating that the user is authorized to have access to the medications stored within the storage device) to the time the user logs out of the system (which may require, e.g., a log-out event by the same user or resulting from an expiration of a predetermined period of time, or a log-in event by a different user for access to the storage device) may define the interaction, whereas the time it takes for the user to remove medications relating to a particular patient may define the removal transaction. A user may conduct multiple removal transactions for multiple patients in a single user interaction with the storage device, and the storage device 5 can be configured to illuminate one or more storage compartments associated with each removal transaction, as discussed below. Additionally or alternatively, the storage device 5 can be configured to illuminate one or more storage compartments associated with any other type(s) of transaction, including counting transaction, stocking transaction, etc.

In some embodiments, one or more lasers and/or other light emitting devices may be configured to facilitate the illumination of, for example, a medication storage compartment by projecting light onto one or more portions of the storage device 5. The light projected onto the portion(s) of the medication storage device may facilitate one or more removal transactions from the storage device 5 by guiding the user to the proper portion of the storage device (e.g., by "highlighting" a particular portion) and/or by displaying user-understandable information (e.g., letters, numbers, symbols, etc.). For example, the projected light can highlight a particular pocket that is to be accessed next by a user. As another example, the projected light can cause information to be displayed onto the medication storage compartment and/or other portion of the storage device. In embodiments where information is projected onto the pocket, for example, the storage device 5 may be able to communicate the information to the user without the need for the user to consult the touch-screen interface (e.g., display device 20) and/or in the absence of any other functioning user interface. In some embodiments, the projected information and/or highlighting light may complement the information displayed by display device 20 and/or other types of user interface components.

Projecting light onto the pocket (and/or any other component of the storage device 5) may also be used instead of or in addition to light emitting components integrated in the drawers and/or other components of the storage device 5. For example, the storage device 5 can be configured to project light from a first location that is external to the drawer and/or any other storage compartment onto a pocket and/or other component of the storage device 5 instead of or in addition to including pocket indicators and/or drawer level displays that may be located in or around storage compartments of the storage device 5. Examples of drawer level displays, which may be used in conjunction with the projection functionality discussed herein, are provided in commonly-assigned U.S. patent application Ser. No. 13/076,762, filed Mar. 31, 2011, titled "STORAGE DEVICES, SYSTEMS, AND METHODS FOR FACILITATING MEDICATION DISPENSING AND RESTOCKING," which is hereby incorporated by reference in its entirety. Furthermore, projecting light (as a highlighting means and/or as an information displaying means) on a pocket of the storage device 5 may enable the partial or complete (depending, for example, on the transaction and/or configuration of the storage device 5) elimination of the need for the nurse to consult the touch-screen during at least some types of interactions with the storage device 5. In this regard, some embodiments that include projecting light onto components of the storage device 5 may increase the user workflow speed and/or reduce the likelihood of a user inadvertently stocking or removing a medication in/from an incorrect compartment.

To enable the storage compartments and/or other components as projection screens, storage device 5 may also include one or more light projectors, such as projection box 25 and/or projection bars 30. Additional examples regarding projection box 25 are discussed in connection with, e.g., FIG. 2, and additional examples regarding projection bars 30 are discussed in connection with, e.g., FIG. 3. Furthermore, example methods of using projection box 25 and/or projection bars 30 are discussed in connection with FIGS. 7 and 8.

Additionally, some embodiments of the storage device 5 may include display device 20, which may include a monitor, as depicted in FIG. 1, and may be configured to present various user-understandable information. The display device 20 may include one or more display screens that may also be configured to function as input devices, as noted above. For example, display device 20 may include touch-sensitive components and associated hardware, software and/or firmware. The display device 20 may also be configured to present one or more display screens and/or include one or more cameras and associated hardware, software and/or firmware, such as the examples provided in commonly assigned U.S. patent application Ser. No. 13/235,178, filed Sep. 16, 2011, titled "SYSTEMS, METHODS AND COMPUTER PROGRAM PRODUCT FOR MONITORING INTERACTIONS WITH A MEDICATION STORAGE DEVICE," which is hereby incorporated by reference in its entirety. In embodiments of the storage device 5 that include cameras, the cameras can be configured to assist in the calibration of the light projectors discussed herein (e.g., projection box 25 and/or projection bars 30) by, e.g., determining how accurately the light being projected is illuminating the portion of storage device 5 that it is intended to be illuminated. Other examples of user output components that may be included in the storage device 5 include lights, audio speakers, haptic feedback components, and/or any other component that may generate stimuli detectable by a user.

As such, the user input and output devices (including projection box 25 and/or projection bars 30) may be configured to help facilitate particular removal, stocking and/or counting transactions. For example, a user input device may receive input in the form of identification credentials authorizing the user to access the storage device 5 and/or a particular drawer 10 of the storage device 5; a selection of a patient for whom medication is to be dispensed; a request for information regarding a particular medication stored in one of the drawers or a particular patient to whose records the user has access; a selection of a particular medication to be viewed or dispensed; and so on. User output devices may then help direct the user to the appropriate storage compartment (e.g., drawer, pocket, and/or any other medication storage component of the storage device 5) from which the medication can be removed. Furthermore, in some cases, the storage device 5 may be configured to communicate with other storage devices and/or other types of machines, as discussed in connection with FIG. 6, such that the user may be able to enter input requesting information regarding the contents of the other storage devices.

For example, using the display device 20, the user may be able to view a list of patients under the user's care; view patient details (e.g., patient's name, date of birth, medical condition, allergies, date of admittance, date of expected discharge, etc.); view a list of prescribed medications for a particular patient; view medication details (such as potential interactions, medication properties, and dosage information); and/or view order details (such as the name of a medication, required dosage, quantity to be dispensed, portion of the medication in the storage device, etc.). Some or all of the user's interactions at the storage device 5 may be monitored at a remote machine and/or recorded at the storage device and/or at a remote machine. Additionally or alternatively, any information presented by the display device 20 may also be presented on any other component of the storage device 5 using one or more projectors discussed herein.

Different types of storage devices 5 may include different sizes and styles of drawers 10, depending on, for example, the types of medications to be stored in the drawers 10, the quantities required (which may be dictated by the size or type of the facility or other area serviced by the automated storage device), and user preferences. For example, as shown in FIG.

1, some of the drawers 10 may be relatively deep, whereas others may be relatively shallow. As another example, the number, arrangement and size of the pockets and/or other types of storage type compartment(s) included in one of the drawers 10 may be different than that included in another of the drawers 10. Despite the various arrangements of the drawers 10, projection box 25 and/or projection bars 30 can be configured to visually highlight and/or project information onto one or more specific storage compartments included in one or more of drawers 10, as described in greater detail below. In some embodiments, the storage compartment(s) can be made of materials and/or otherwise configured (e.g., include structure elements, like ribs and textured surfaces) that enhance or otherwise facilitate their illumination by one or more projectors, such as those discussed herein.

Additionally or alternatively, each storage compartment may also be locked with a lid that the storage device 5 can be configured to unlock only when medication stored in the particular pocket is to be dispensed, restocked and/or counted. For example, each drawer 10 and/or compartment may be in a locked state until an authorized user interfaces with the storage device 5 to access a particular drawer, pocket and/or other storage compartment, at which point the storage device may unlock and/or open the compartment to allow the user's access. In some cases, the compartment and/or other component of the storage device may have an opaque or other type of cover that aids in enabling the component to function as a display screen for the projectors discussed herein. For example, the configuration (e.g., materials, structural design features, etc.) of the lid (and/or any other portion) of the storage device 5 can help enhance the display of information projected by one or more of the projection box 25, projection bars 30 and/or any other projector located external to that onto which the light is being projected. In some embodiments, rather than or in addition to displaying information, the compartment and/or other component of the storage device can simply be highlighted using a light projected by projection box 25 and/or projection bars 30.

The storage device 5 may also include one or more other components and/or provide one or more other functions not specifically shown in the drawings (to avoid overcomplicating the drawings unnecessarily). For example, the storage device 5 may include a container dispensing device mounted to or otherwise supported by the storage device. The container dispensing device may be configured to store and dispense containers, and each container may be configured to receive one or more dispensed medications for administering to a single selected patient. Thus, each container may be configured to allow the secure transport of the dispensed medications received therein between the storage device 5 and the selected patient's bedside.

Figure 2:
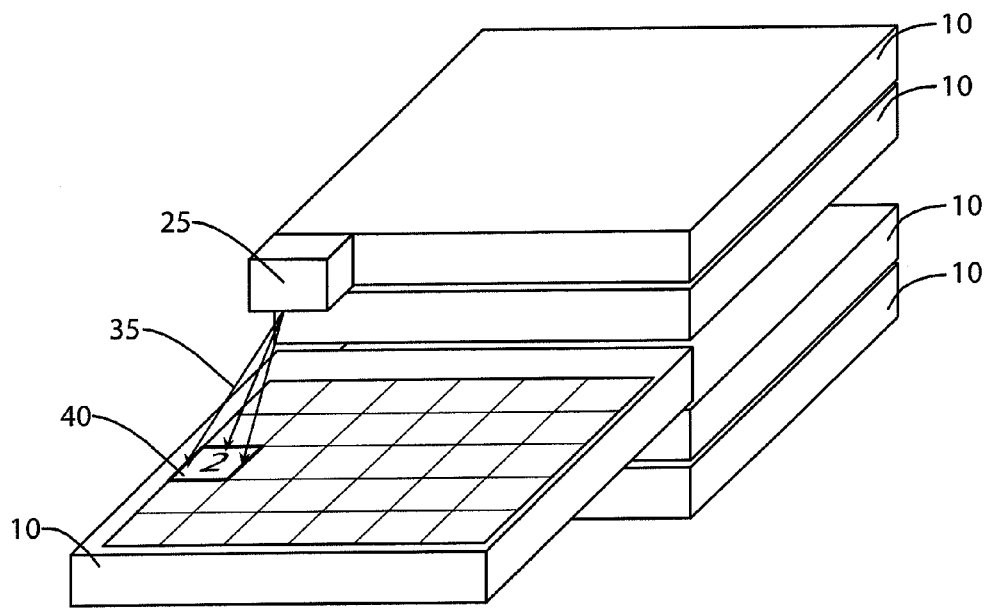
FIGS. 2 and 2A illustrate a first type of example projector that can be configured to provide directing light and may be included in automated storage devices in accordance with some example embodiments discussed herein.

Turning next to FIG. 2, projection box 25 may include one or more light emitting devices that may be controlled by circuitry (such as a processor of storage device 5 and/or a processor included within the projection box 25) to project light 35 onto one or more components, such as pocket lid 40, of drawer 10. Light 35 may include, among other things, laser light, visible light, infrared light and/or any other suitable form of light. For example, a laser light source can be used that emits standard low-intensity laser beams similar to or the same as those used in other applications (such as, e.g., laser pointers, laser levels, laser thermostats, etc.). In some embodiments, for example, light 35 may be directed at one or more particular areas of drawer 10, such that light 35 highlights, guides the user to and/or otherwise indicates one or more correct pocket locations that are to be accessed by the user for various reasons (e.g., remove medications, stock supplies, conduct a blind count, etc.). For example, projection box 25 may be configured to direct the light 35, such that the light 35 is projected onto only one component of drawer 10 at a time (as shown in FIG. 2), and/or be configured to highlight a plurality of components of drawer 10 simultaneously (or near-simultaneously, including seeming to the user to appear simultaneously). Any suitable means can be included in projection box 25 that allows for the directing of light, such as one or more movable mirrors and/or other light reflecting components that can be configured to be controllably moved by circuitry (such as a processor included in storage device 5) and direct the light emitted by the projecting component(s).

Figure 2A:
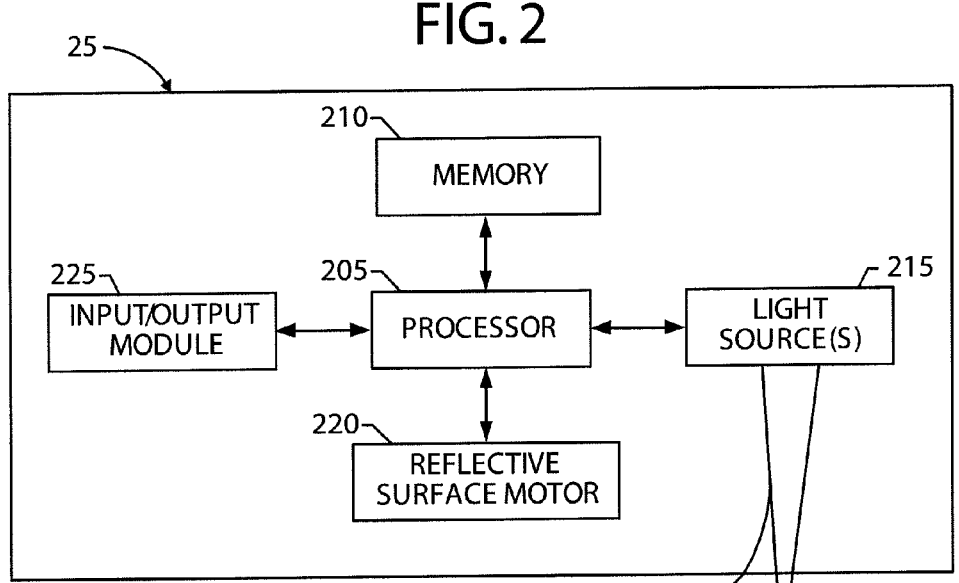

For example, as shown in FIG. 2A, projection box 25 may include processor 205 that may, for example, be embodied as various means including one or more microprocessors with accompanying digital signal processor(s), processor(s) without an accompanying digital signal processor, one or more coprocessors, multi-core processors, controllers, computers, various other processing elements including integrated circuits such as, for example, an ASIC (application specific integrated circuit) or FPGA (field programmable gate array), or some combination thereof. Accordingly, although shown in FIG. 2A as a single processor, in some embodiments the processor 205 comprises a plurality of processors and/or any other type of control circuitry. The plurality of processors, for example, may be embodied on a single computing device or may be distributed across a plurality of computing devices collectively configured to function as the processor 205. The plurality of processors may be in operative communication with each other and may be collectively configured to perform one or more functionalities of the processor 205 as described herein. In an example embodiment, the processor 205 is configured to execute instructions stored in the memory 210 and/or that are otherwise accessible to the processor 205.

The memory 210 can be in communication with and/or included in the processor 205. The memory 210 may comprise volatile and/or non-volatile memory that stores content, data and/or any other information. For example, the memory 210 can store information generated by, transmitted from, and/or received by, the projection box 25. Also for example, the memory 210 can store software applications, firmware, instructions and/or the like for the processor 205 to perform steps associated with operation of the projection box 25. For example, the memory 210 may be a non-transitory storage medium that stores computer program code comprising instructions or other executable portions that the processor 205 executes to perform the steps described above and below with regard to, e.g., FIGS. 7 and 8.

These instructions, when executed by the processor 205, may cause the projection box 25 to perform one or more of the functionalities described herein. As such, whether configured by hardware, firmware/software methods, or by a combination thereof, the processor 205 may comprise an entity capable of performing operations according to embodiments of the present invention while configured accordingly. Thus, for example, when the processor 205 is embodied as an ASIC, FPGA or the like, the processor 205 may comprise specifically configured hardware for conducting one or more operations described herein. Alternatively, as another example, when the processor 205 is embodied as an executor of instructions, such as may be stored in the memory 210, the instructions may specifically configure the processor 205 to perform one or more algorithms and operations described herein.

For example, the memory 210 may include instructions for controlling one or more light sources 215 and/or reflective surface motors 220. Upon being executed, the instructions may, for example, cause one or more light sources 215 to direct certain types of light in a particular manner, including causing the movement of mirrors (using reflective surface motors 220) and/or the adjusting of aperture(s), among other things.

In other embodiments, one or more of the components shown in FIG. 2A (and/or any other drawing discussed herein) may be omitted and/or the functionality associated therewith may be performed by another component discussed herein. For example, the functionality discussed in connection with processor 205 may be performed by processor 505 of FIG. 5 discussed below. As another example, the instructions executed by processor 205 may be based on data stored in memory 510 of FIG. 5, as opposed to or in addition to data stored on memory 210.

Light sources 215 may include, for example, a single standard laser beam (such as a laser pointer) that can be used to cast a single beam of light (e.g., light 35) onto the lid 40, as shown in FIG. 2. Similarly, the laser beam and/or other type of light may be projected onto open matrix pockets that do not include a lid (not shown). In such embodiments, one or more of the open matrix pockets can comprise various materials, structure features and/or other configurations that enhance the illumination caused by light sources 215. For example, if light source 215 is an ultraviolet laser beam, lid 40 and/or open matrix pockets can comprise a material that fluoresces in the presence of ultraviolet light.

As another example, light sources 215 may include a plurality of laser beams (e.g., four laser beams). Additionally or alternatively, each of light sources 215 may include one or more optical components that can split and/or otherwise influence the light 35 such that it may be used to highlight and/or project information simultaneously onto one or more open pockets and/or lidded compartments, among other things. The plurality of laser beams (and/or parts of a split laser beam) can also or instead be used to outline a pocket. To gain an outlined image of a pocket and/or other component of the storage device 5, a plurality of lasers may be incorporated in light sources 215 and/or light sources 215 may include or project through a square filter (and/or other type of optical component(s)) to achieve the outlining effect.

In addition to or instead of outlining and/or otherwise highlighting a component of the storage device 5, information may be projected onto a component of storage device 5. For example, as shown in FIG. 2, the number "2" may be projected onto lid 40, thereby indicating to the user that 2 doses of medication should be removed from the pocket associated with lid 40 during the next removal transaction. In some embodiments, projection box 25 can be configured to project any type of information (including user-understandable characters, words, symbols, images, etc.) onto one or more components of storage device 5 (including into a pocket, on a side wall of a pocket, on the bottom of a pocket, across multiple pockets, among other places).

For example, to project various information, projection box 25 may also or instead include a non-laser light source in light sources 215, such as a mini-projector (e.g., a pico projector), which can be configured to cast dynamically changing data onto one or more pockets and/or other components of the storage device 5. In this regard, projection box 25 may include components similar or the same as those sometimes used in a heads-up-display ("HUD") used in aircraft and terrestrial vehicles.

The drawers 10 and/or other components of the storage device 5 can also include one or more components that assist in functionality of projection box 25. In some embodiments, sensors mapped to the pockets in each drawer can be included, which may enable the highlighted pocket to be illuminated correctly. For example, the sensors may include a progression sensor that enables processor 205 to cause light 35 to follow the pocket dynamically by, e.g., controlling light sources 215 and/or reflective surface motor 220. As another example, the sensors may be configured to determine when the drawer is fully extended, thereby enabling the circuitry in the storage device to know at least the proximate location of various components of one or more drawers 10 relative to the location of the projection box 25 on the storage device 5. In other words, the sensors may be used by the circuitry of the storage device 5 to triangulate and/or otherwise calculate the relative position of one or more components of the drawers 10 that are to be highlighted and/or otherwise used as a projection screen.

In some embodiments, projection box 25 may also be able to move on the storage device 5. For example, projection box 25 may be mounted on a track and/or other apparatus that allows projection box 25 to move in one or more directions relative to the drawers 10. Although such motors are not discussed in connection with FIG. 2A, those discussed in connection with FIG. 3A may be used in conjunction with projection box 25. Furthermore, other aspects of various embodiments may be combined, substituted and/or rearranged, among other things, without departing from the spirit of the invention.

In some embodiments and further to the above discussion, the lid 40 and/or other component of the storage device 5 can be configured to aid in facilitating the display of information projected by projection box 25. For example, the lid can be opaque (rather than translucent) and/or otherwise made from one or more materials that enable the display of information. As another example, one or more portions of the storage device 5 can comprise material that fluoresces when exposed to one or more particular wavelengths of light (such as ultraviolet light and/or infrared light), which may allow projection box 25 to use various wavelengths of light to highlight and/or display various information on components of the storage device 5.

The processor 205 can also be configured to communicate directly and/or indirectly with other components and/or machines discussed herein. In some embodiments, one or more input and/or output modules, such as input/output module 225 may enable processor 205 to interface with the circuitry discussed in connection with FIGS. 3A and/or 5. The input/output module 225 may include specialized circuitry, one or more ports (serial, such as universal serial bus "USB" ports, and/or parallel ports), any wired or wireless communication network components (including those for WiFi, BlueTooth®, among others), and/or any other component that facilitates the reception and/or transmission of signals from/to one or more other components. In this regard, the input/output module 225 can facilitate the functionality of the projection box 25. Although more than one input/output module 225 can be included in the storage device 5, only one is shown in FIG. 2A to avoid overcomplicating the drawing (like the other components discussed herein).

Figure 3:
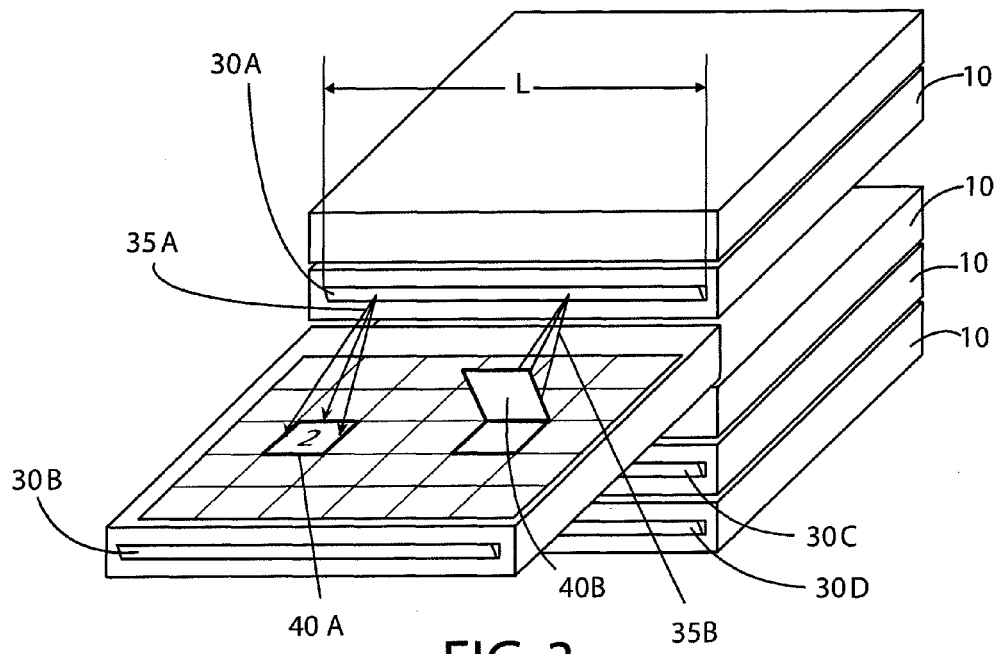
FIGS. 3 and 3A illustrate a second type of example projector that can be configured to provide directing light and may be included in automated storage devices in accordance with some example embodiments discussed herein.
Figure 3A:
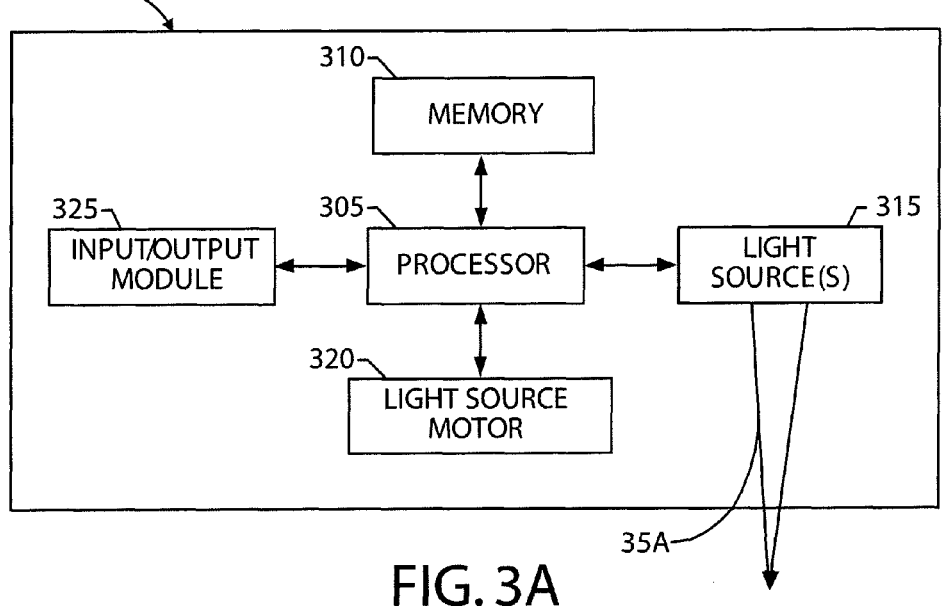
Figure 4:
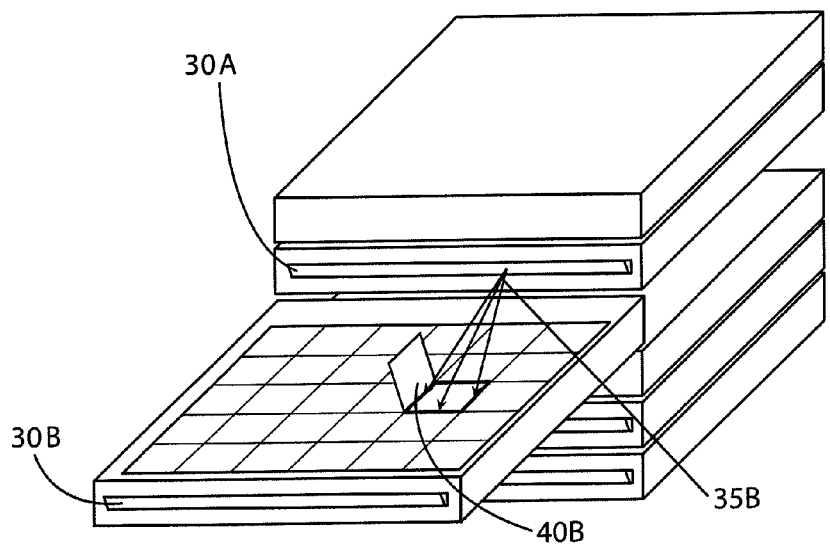
FIG. 4 illustrates an example of a modified drawer that includes a pocket having a lid that does not obstruct the directing light emitted by an example projector in accordance with some example embodiments discussed herein.

FIGS. 3-4 show example embodiments that include projection bars 30A-30D, among other components. One or more of the components shown in FIGS. 3 and/or 4 can be combined with components discussed in connection with the other drawings.

Projection bars 30A, 30B, 30C and/or 30D may each include a processor 305, memory 310, light sources 315 and input/output module 325, which may be the same as or similar to their respective components discussed in connection with projection box 25.

The light sources 315 may be located in a single row or multiple rows along the length, "L," of one or more of the projection bars 30A-30D. For example, a first light emitting component included in projection bar 30A can be configured to project light 35A onto lid 40A, and a second light emitting component included in projection bar 30A can be configured to project light 35B onto lid 40B. Additionally or alternatively, each light emitting component included in one or more of the projection bars 30A-30D can include optics and/or other components (such as those that may be used in accordance with projection box 25) that may influence the light emitted by the light emitting components included in projection bars 30A-30D.

Light source motor 320 may also or instead be included in one or more of projection bars 30A-30D. Light source motor 320 may be configured to move one or more of the light emitting components, represented by light sources 315, along the length L and/or otherwise within projection bars 30A-30D. In this regard, for example, the beam of projected light 35A may move along length L of projection bar 35A in response to light source motor being instructed to do so by processor 305.

Lids 40A and 40B may be similar to or the same as lid 40 discussed in connection with FIG. 2. In this regard, projection bars 30A-30D can be configured to project light 35A and/or 35B onto the drawer 10 located directly below. In some embodiments, when the lid is open, as shown by lid 40B in FIG. 3, the lid 40 may block the beam of light (e.g., light 35B) that illuminates the lid 40 when it is in the closed position. To enable light to continue to highlight or otherwise project onto a pocket (and/or other component of the storage device 5) while in an open position, one or more of the lids of one or more drawers 10 can open in a manner that does not obstruct the projection of light 35B and/or any other light being emitted by any projector (e.g., projection box 25 and/or projection bars 30A-30D). For example, lid 40B can be configured to open in a direction orthogonal to the movement of drawer 10 as shown in FIG. 4.

Figure 5:
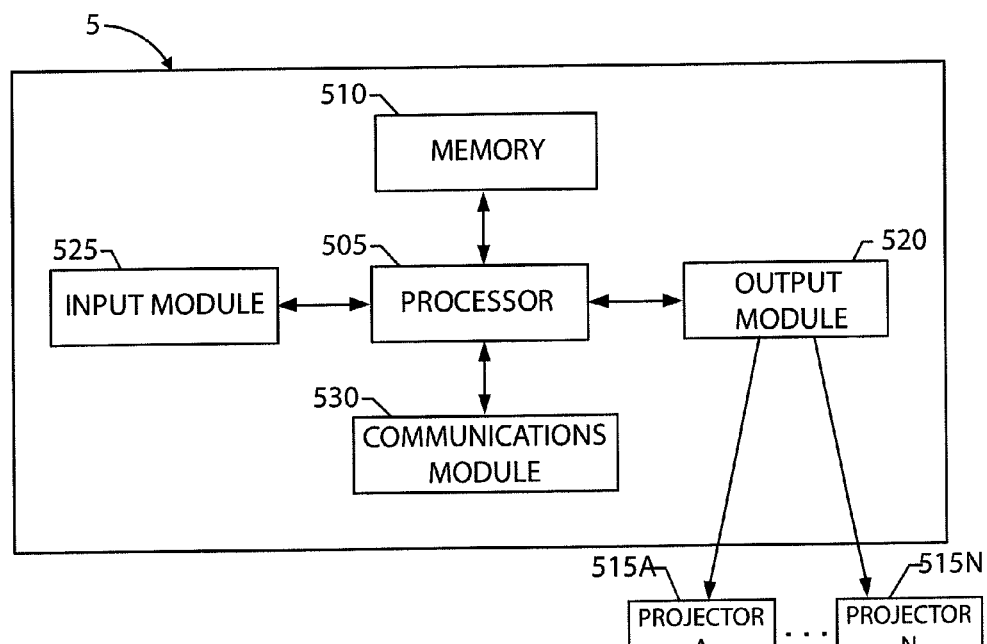
FIG. 5 illustrates a block diagram of circuitry of an apparatus that may be included in some embodiments discussed herein.

Referring now to FIG. 5, the storage device 5 may include any type of circuitry to facilitate the functionality discussed herein. For example, circuitry commonly found in various computing devices and other types of machines (e.g., desktop computer, laptop computer, tablet, etc.), may be included in the storage device 5. To illustrate this, FIG. 5 shows a block diagram of example circuitry components that may be configured to store and/or execute computer-readable program code portions comprising executable instructions and/or other types of executable portions. As such, the storage device 5 may include various means for performing one or more functions in accordance with some embodiments, including those more particularly shown and described herein. It should be understood, however, that the storage device 5 may include alternative means for performing one or more like functions, without departing from the spirit and scope of embodiments discussed herein. As shown, the storage device 5 is a machine and can generally include means, such as processor 505 for performing or controlling the various functions of the storage device 5.

The processor 505 may, for example, be embodied as various means including one or more microprocessors with accompanying digital signal processor(s), processor(s) without an accompanying digital signal processor, one or more coprocessors, multi-core processors, controllers, computers, various other processing elements including integrated circuits such as, for example, an ASIC (application specific integrated circuit) or FPGA (field programmable gate array), or some combination thereof. Accordingly, although shown in FIG. 5 as a single processor, in some embodiments the processor 505 comprises a plurality of processors and/or any other type of control circuitry. The plurality of processors, for example, may be embodied on a single computing device or may be distributed across a plurality of computing devices collectively configured to function as the processor 505. The plurality of processors may be in operative communication with each other and may be collectively configured to perform one or more functionalities of the processor 505 as described herein. In an example embodiment, the processor 505 is configured to execute instructions stored in the memory 510 and/or that are otherwise accessible to the processor 505.

The memory 510 can be in communication with and/or included in the processor 505. The memory 510 may comprise volatile and/or non-volatile memory that stores content, data and/or any other information. For example, the memory 510 can store information generated by, transmitted from, and/or received by, the storage device 5. Also for example, the memory 510 typically stores software applications, instructions or the like for the processor 505 to perform steps associated with operation of the storage device 5. For example, the memory 510 may be a non-transitory storage medium that stores computer program code comprising instructions or other executable portions that the processor 505 executes to perform the steps described above and below with regard to, e.g., FIGS. 7 and 8.

These instructions, when executed by the processor 505, may cause the storage device 5 to perform one or more of the functionalities described herein. As such, whether configured by hardware, firmware/software methods, or by a combination thereof, the processor 505 may comprise an entity capable of performing operations according to embodiments of the present invention while configured accordingly. Thus, for example, when the processor 505 is embodied as an ASIC, FPGA or the like, the processor 505 may comprise specifically configured hardware for conducting one or more operations described herein. Alternatively, as another example, when the processor 505 is embodied as an executor of instructions, such as may be stored in the memory 510, the instructions may specifically configure the processor 505 to perform one or more algorithms and operations described herein.

For example, the memory 510 may include instructions for controlling one or more projectors 515A though 515N, such that one or more specific portions of the storage device 5 are illuminated (e.g., highlighted and used as an information display screen). The projectors 515A-515N may include, for example, at least one projection box 25 and/or projection bars 30A-30D. Upon being executed, the instructions may, for example, cause one or more light emitting components of the one or more projectors 515A-515N to direct certain types of light in a particular manner, including causing the movement of mirrors and/or the adjusting of aperture(s), among other things, some examples of which are discussed above. As another example, the memory 510 may store instructions that enable information to be presented by the display device 20.

The processor 505 can be configured to communicate directly with the projectors 515A though 515N. In some embodiments, one or more output modules, such as output module 520 may enable processor 505 to interface with projectors 515A though 515N. The output module 520 may include specialized circuitry, one or more ports (serial, such as universal serial bus "USB" ports, and/or parallel ports), and/or any other component that facilitates the output of signals to one or more output components, such as projectors 515A though 515N, a speaker, a different light emitting device, display device 20, etc. In this regard, the output module 520 can facilitate the functionality of one or more user interfaces and, in turn, provide information to a user using any number and/or types of devices. Although more than one output module 520 can be included in the storage device 5, only one is shown in FIG. 5 to avoid overcomplicating the drawing (like the other components discussed herein).

In addition to or instead of executing the instruction stored on the memory 510, the processor 505 may be configured to receive a signal from the input module 525, which may include specialized circuitry, one or more ports (serial, such as universal serial bus "USB" ports, and/or parallel ports), and/or any other component that facilitates the reception of signals from an input component. In some embodiments, the input module 525 can function as a user input interface and, in turn, receive data from any of a number and/or types of devices and/or users. For example, the input module 525 may be electrically coupled to the display device 20, the user input device 15 and/or the user input device 25. Similarly, one or more image capturing devices may be coupled to input module 525. Although more than one input module 525 can be included in the storage device 5, only one is shown in FIG. 5 to avoid overcomplicating the drawing (like the other components discussed herein).

As discussed below (in connection with, e.g., FIG. 6), the storage device 5 may be connected to a network and be configured to interface with one or more remote machines, such as data servers, databases, administrator machines, tablets, cellular devices, other mobile devices, etc. To facilitate this functionality, the memory 510 may also include instructions that are executable by the processor 505. The processor 505 can also be configured to utilize the communications module 530 to communicate with one or more remote machines (e.g., via a network, such as that discussed in FIG. 6). The communications module 530 can include hardware, software, and/or any other means for transmitting and/or receiving data, content or any other type of information from a network or other type of device.

Figure 6:
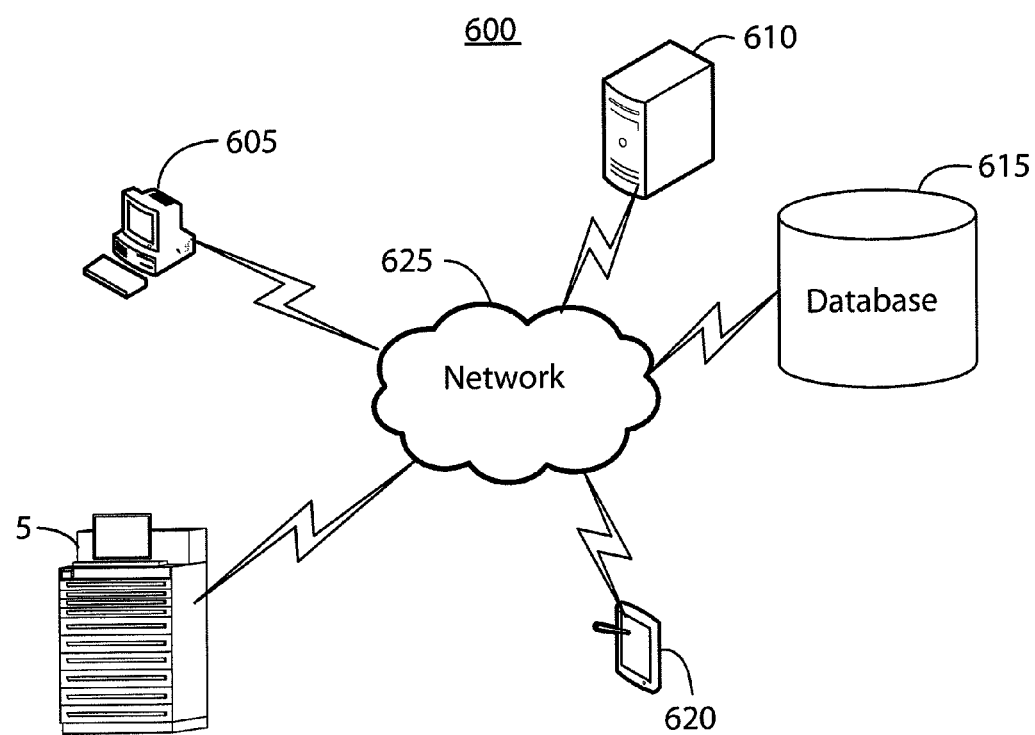
FIG. 6 illustrates an example system diagram in accordance with some embodiments discussed herein.

Referring to FIG. 6, system 600 is shown as an exemplary networked system that may benefit from embodiments provided herein. In addition to the storage device 5, system 600 may further include administrative machine 605, central server 610, database 615, mobile device 620, and network 625. The system 600 can be associated with a healthcare department, healthcare facility and/or entire enterprise in which the storage device 5 and/or other types of medication storage devices are being used or available for use. The storage device 5 may use the communications module 530 to access the network 625 and the other devices attached thereto, including the central server 610, in order to provide and/or receive data signals (such as, e.g., commands to remotely control, troubleshoot and/or calibrate the projection devices, etc.). The network 625 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.).

In response to receiving data from the storage device 5, the central server 610 may process and/or provide the data to the administrative machine 605, database 615, the mobile device 620, and/or any other networked devices (not shown) that may be used to view, store and/or otherwise process the data. For example, database 615 may store data associated with one or more medication storage devices including, for example, configuration data, calibration data, metadata, storage device name, storage device portion, types of medication being stored, remaining quantities of medication being stored, whether the device is in-use or available, user identifying information associated with the current user and/or previous user(s) of the device, error information (including, e.g., the type of error and the time the device went into the error state), and/or any other information that may be related to the use of the storage device 5 and/or any other machine included in system 600. In an alternative embodiment, some or all of the additional information associated with each of the medication storage devices may be stored in memory associated with each of the medication storage devices (e.g., the storage device 5), which central server 610 and/or the other medication storage devices can be configured to access, thus eliminating the need for database 615.

The administrative machine 605 can be any type of computing device, such as a personal computer, that can be configured to receive, process and/or present to a user some or all of the data generated by the storage device 5 and/or control the functionality of the storage device 5, including controlling, configuring and/or troubleshooting projection-related components included in the storage device 5. For example, the administrative machine 605 can be used to upload new firmware and/or software onto the storage device 5 that is used to control the projector(s) (e.g., projection box 25 and/or projection bars 30) included in the storage device 5.

The mobile device 620 and/or any other type of device can also be configured to function the same as and/or provide similar or a subset of the functionality discussed in connection with the administrative machine 605. The mobile device 620 may be a tablet device, personal digital assistant, cellular phone, any other type of mobile device, or combination thereof.

Figure 7:
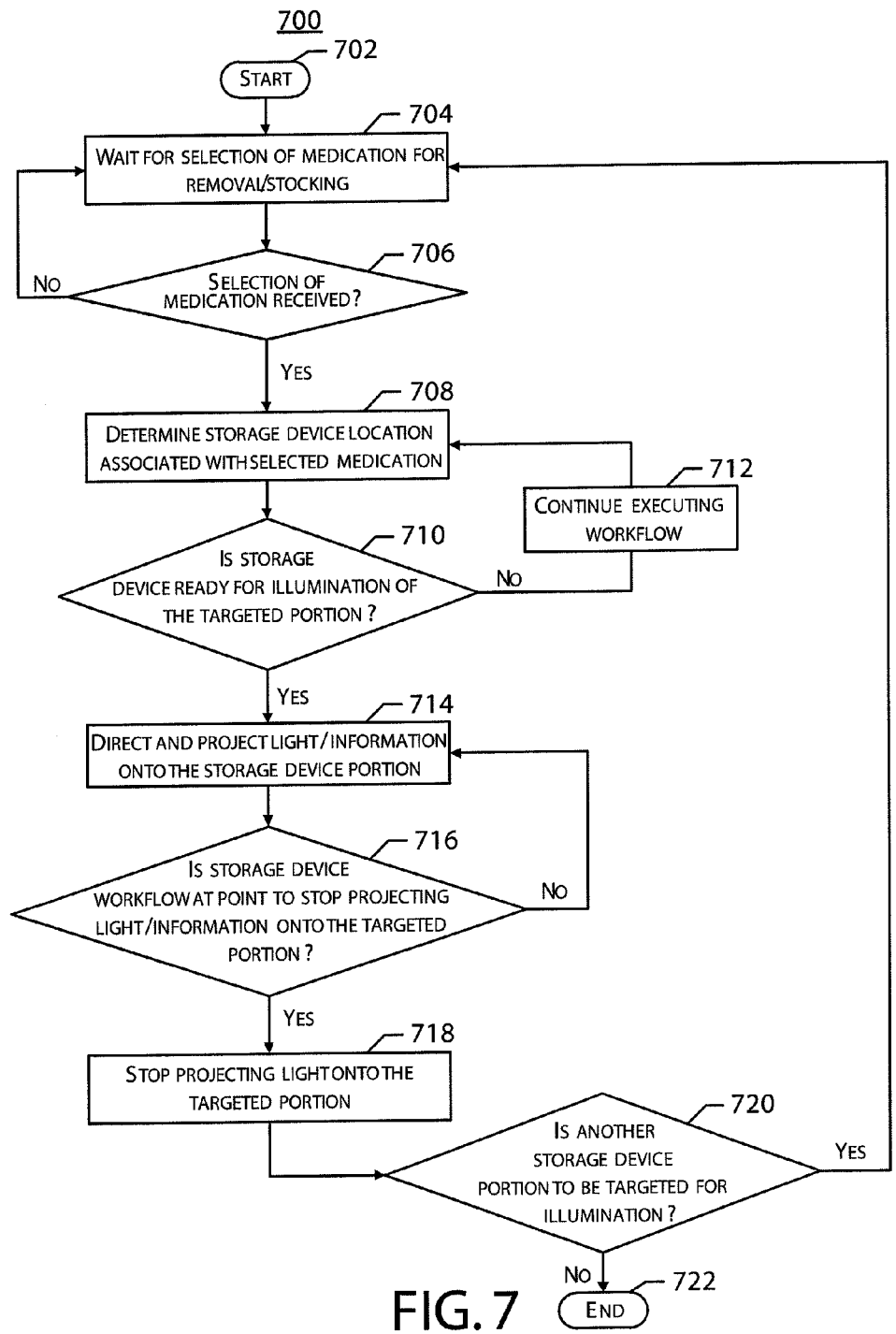
FIGS. 7-8 are example flowcharts illustrating operations that can be performed in accordance with some embodiments of discussed herein.
Figure 8:
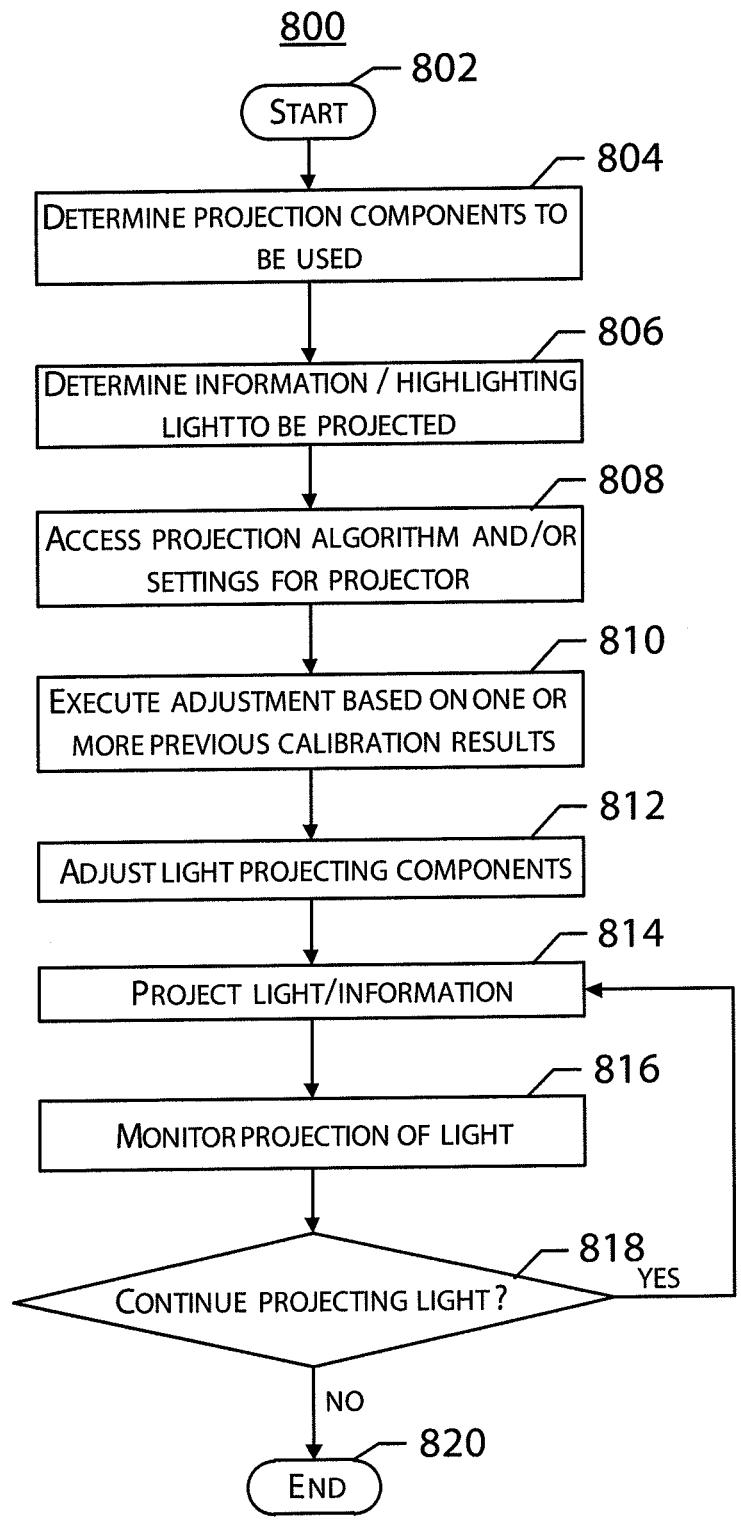

FIGS. 7 and 8 show processes 700 and 800, respectively, which may be used in accordance with some embodiments to project light and/or information on one or more components of a storage device, such as storage device 5 discussed herein. Processes 700 and 800 are represented by flow diagrams in accordance with some exemplary methods, computer program products and/or systems discussed herein. It will be understood that each operation, action, step and/or other types of functions shown in the diagrams, and/or combinations of functions in the diagrams, can be implemented by various means. Means for implementing the functions of the flow diagrams, combinations of the actions in the diagrams, and/or other functionality of example embodiments of the present invention described herein, may include hardware and/or a computer program product including a computer-readable storage medium (as opposed to or in addition to a computer-readable transmission medium) having one or more computer program code instructions, program instructions, or executable computer-readable program code instructions stored therein. For example, program code instructions associated with FIGS. 7 and 8 may be stored on one or more storage devices, such as memory 210, 310 and/or 510, and executed by one or more processors, such as processors 205, 305 and/or 505. Additionally or alternatively, one or more of the program code instructions discussed herein may be stored and/or performed by distributed components, such as those that may be connected to storage device 5 via a network or other communications interface. As will be appreciated, any such program code instructions may be loaded onto computers, processors, other programmable apparatuses (e.g., storage device 5) or network thereof from one or more computer-readable storage mediums to produce a particular machine, such that the particular machine becomes a means for implementing the functions of the actions discussed in connection with, e.g., FIGS. 7, 8 and/or the other drawings discussed herein.

The program code instructions stored on the programmable apparatus may also be stored in a non-transitory computer-readable storage medium that can direct a computer, a processor (such as processors 205, 305 and/or 505) and/or other programmable apparatus to function in a particular manner to thereby generate a particular article of manufacture. The article of manufacture becomes a means for implementing the functions of the actions discussed in connection with, e.g., FIGS. 7 and 8. The program code instructions may be retrieved from a computer-readable storage medium and loaded into a computer, processor, or other programmable apparatus to configure the computer, processor, or other programmable apparatus to execute actions to be performed on or by the computer, processor, or other programmable apparatus. Retrieval, loading, and execution of the program code instructions may be performed sequentially such that one instruction is retrieved, loaded, and executed at a time. In some example embodiments, retrieval, loading and/or execution may be performed in parallel by one or more machines, such that multiple instructions are retrieved, loaded, and/or executed together. Execution of the program code instructions may produce a computer-implemented process such that the instructions executed by the computer, processor, other programmable apparatus, or network thereof provides actions for implementing the functions specified in the actions discussed in connection with, e.g., process 700 of FIG. 7.

Process 700 starts at 702 and proceeds to 704 where the storage device waits for a selection (e.g., user selection, automatic selection or combination thereof) of one or more medications for removal from, inventory of and/or stocking into the storage device. For example, the user may have to first login to the system by providing various identifying credentials (e.g., username and password), and progress through the workflow of the storage device's user interface system before a selection of one or more medications for stocking and/or removal can be made. In other words, in some embodiments, while the user is interacting with the storage device in a manner other than removing, taking inventory of and/or stocking medication(s) (but not limited to these tasks), the projection functionality of the storage device may wait at 704 to be activated.

At 706 a determination is made as to whether or not a selection of a medication to be removed and/or stocked has been made. In response to determining no medication has been selected yet, process 700 returns to 704 and continues to wait.

In response to determining at 706 that the processor has received an indication of a medication to be selected for dispensing or stocking (e.g., receiving an indication of a user selecting a medication identifier presented on display device 20), process 700 can be configured to proceed to 708.

At 708, a determination is made as to where in the storage device the medication is to be stored and/or removed from. For example, a determination can be made at 708 as to the relative and/or absolute location of a pocket, medication storage compartment and/or other storage device portion associated with the selected medication. In some embodiments, the storage device can begin executing at 708 one or more projection algorithms, including retrieving the projection algorithms and/or projection settings from memory and storing any results calculated in memory. In other embodiments, one or more of the functionalities discussed in connection with 708 may occur later in process 700 (e.g., at 714).

For example, at 708 the storage device can be configured to utilize relative location algorithms that may include inputting one or more projection settings into one or more projection algorithms that can be used to determine a target portion relative to a known location of a storage device component. For example, a first pocket may be used as a default position and other pockets may be illuminated based on their position relative to the known pocket. In embodiments that include projection box 25, for example, to shine on a pocket to the left of the known pocket location, the system can execute an algorithm that causes it to direct a mirror (included in projection box 25) 5 degrees to the left relative to the position the mirror would be used for the known pocket location. As another example, each storage device portion (e.g., pocket and/or other type of compartment) may be independently preprogrammed into the storage device in terms of, for example, mirror angles, aperture settings, light intensity, power output and/or other projector-related settings (sometimes referred to herein as "projection settings"). The various projection settings and/or projection algorithms (into which the projection settings are inputted) can be dependent on the types, locations, and/or other characteristics of the one or more projectors included in the particular storage device(s) configured to implement process 700, and the projection settings and/or projection algorithms can be stored locally within the storage device(s) (e.g., in memory 510) and/or remotely (e.g., in database 615).

At 710, a determination can be made whether or not the storage device is at a point in its workflow in which light is to be directed and projected. For example, the projecting functionality discussed herein (e.g., projecting a highlight and/or information carrying beam of light) may not be triggered until the storage device determines that the drawer containing the pocket to be highlighted is in the fully extended position. The amount a drawer is open may, in some instances, effect the configuration needed by the projector to illuminate a particular portion of the storage device. For example, the farther a drawer is extended into the open position, the farther away a pocket may be relative to where a light source is mounted onto the storage device. In some embodiments, the processor (and/or other circuitry) of the storage device can be configured to dynamically determine the location of any component of the storage device (including, e.g., using a sensor that measures the distance that a drawer is extended at a given time, such as when the light projector is and/or is about project light). In other embodiments, the drawer and/or other component being in a predetermined position (e.g., fully extended into the open position) may function as a triggering event required to activate the light source(s), as discussed herein. In addition to or instead of determining at 710 the physical location of the storage device component targeted for illumination (with, e.g., a highlighting beam of light and/or information), a determination can be made at 710 as to whether or not the user has reached a point in the user interface workflow at which medication is ready to be stocked and/or removed from the storage device. These are but a few examples of projection triggering events that may need to be satisfied in some embodiments before the projector(s) are activated (e.g., before projection settings are retrieved and/or executed in the projection algorithms, and/or light is illuminated by the light source(s)).

In response to determining at 710 that the storage device is not yet ready for illumination of the targeted storage device portion (e.g., the pocket or other compartment to be interacted with by the user), process 700 proceeds to 712 and continues to execute the workflow of the storage device (e.g., wait for sensors to indicate the drawer is fully extended into the open position, the user to finish interacting with the user interface of the storage device, etc.).

In response to determining at 710 that the storage device is ready for illumination of the targeted storage device portion (e.g., the pocket or other compartment to be interacted with by the user), process 700 proceeds to 714 and activates one or more projectors (e.g., projection box 25 and/or projection bars 30). Activating the one or more projectors may include various sub-algorithms, an example of which is represented by the process flow shown in FIG. 8 discussed below. While the one or more projectors is active, light may be projected onto one or more targeted portions of the storage device without illuminating at least some non-targeted portions. For example, a medication storage pocket of a drawer may be illuminated by the projector, while another medication storage pocket within the same drawer may not be illuminated. These pockets may or may not be adjacent, in some embodiments. As used herein, a lack of illumination could, but does not necessarily mean absolutely no light from the projector is reaching the non-targeted portion of the storage device. Rather, as used herein, the targeted portion(s) of the storage device would receive, for example, at least 95% of the light projected by the projector and the non-targeted portions would receive less than, for example, 5% of the light projected by the projector. In some embodiments, however, a light emitting device can be used that has a contrast ratio of approximately 1000:1 or better. For example, some pico projectors can have such a contrast ratio, wherein "contrast ratio" is defined as the difference between the brightest whites and the darkest blacks on the projected surface. In such instances, a contrast ratio of 1000:1 would translate to a 99.9% amount of light transmitted to the target area (e.g., the pocket being highlighted).

At 716, a determination can be made whether or not the storage device's workflow has progressed to a point where the projector(s) should cease to project light onto the targeted storage device portion. For example, at 716 one or more sensors and/or input components can be periodically polled and/or a determination may be made as to whether one or more predetermined interrupts have been received that indicate to the storage device that the storage compartment (e.g., pocket and/or drawer) has been closed or is being closed. As another example, a determination can be made at 716 whether or not the user has interacted with display device 20 in a manner that indicates the user has finished removing and/or stocking medications within the targeted storage device portion. In response to determining at 716 that light should continue to be projected, process 700 returns to 714.

In response to determining at 716 that the projector should cease projecting light onto the targeted storage device portion, process 700 can proceed to 718 and stop projecting light (e.g., a highlighting beam and/or information) onto the targeted storage device portion.

At 720, a determination can be made as to whether or not another medication is to be removed and/or stocked into another storage device portion. If so, process 700 may return to an early step. Although FIG. 7 shows process 700 returning to 704, process 700 may return to any other step that may be included in process 700, such as 708. In some embodiments, light will continue to be projected by the projector while the next targeted portion is determined. For example, light may continue to be projected while the mirrors and/or other reflective surfaces within the projection box 25 are adjusted to illuminate another targeted area of the storage device 5 and/or while the light source included in projection bar (e.g., 30A-30D) is moved along the length of the projection bar. In some embodiments, the projector(s) can stop projecting light while determining at 720 if there is another storage device portion that is to be illuminated and/or while executing one or more of the other steps of process 700 after determining that there is another storage device portion that is to be illuminated.

Process 700 can end at 720 in response to determining at 720 that there are no other portions of the medication storage device targeted for illumination.

FIG. 8 shows process 800, which is an example of functionality that may be included in some embodiments that include activating one or more projectors, such as projection box 25 and/or projection bars 30 discussed herein. Process 800 starts at 802.

At 804, in embodiments where multiple light sources are included in the storage device (e.g., lasers having different wavelengths in the projection box 25 and/or plurality of projection bars 30 mounted on different drawers), a determination can be made as to which light source(s) should be used to illuminate the targeted storage device portion. As another example, multiple light sources may be used to project information onto and/or highlight the targeted storage device portion. In other embodiments that include only a single light source, step 804 can be omitted (as can any other functionality discussed herein be omitted from some embodiments).

At 806, a determination can be made as to whether or not information and/or highlighting light is to be projected onto the storage device. For example, in some embodiments, the storage device may be configured to shine a light onto one or more pockets that are to be accessed by the user, and/or project user-understandable information (e.g., numbers, words, symbols, etc.) onto the pocket and/or other component of the storage device.

At 808, the projection algorithm and/or projection settings can be accessed from memory and executed. In some embodiments, the projector can be calibrated prior to executing the projection processes discussed herein (e.g., by projecting light and receiving feedback automatically from integrated sensors and/or from user inputs), and at 810 an adjustment based on one or more previous calibration results can be integrated into the projection algorithm.

At 812, the components of the projector(s) can be adjusted to be directed at the targeted storage device portion. For example, reflectors included in projection box 25 can be rotated or otherwise moved to the correct angle of attack. In response to one or more triggering events (some examples of which are discussed in connection with FIG. 7), light can be projected at 814. In some embodiments, one or more sensors may be included in one or more targeted storage device portions, and at 816 the storage device can monitor (e.g., receive and analyze) the light that is projected. The decision made at 818 can be the same as or substantially similar to that discussed in connection with 716 discussed above. Process 800 can end at 820 and, for example, 718 of FIG. 7 may be executed thereafter.

In this regard, embodiments discussed herein can assist in highlighting a compartment and/or other component of a medication storage device for a user. Many modifications and other embodiments of the inventions set forth herein will come to mind to one skilled in the art to which these inventions pertain having the benefit of the teachings presented in the foregoing descriptions and the associated drawings. For example, while the embodiments shown in the drawings illustrate light projectors integrated into the storage device (e.g., projection box 25 and projection bars 30), one or more light projectors may be located anywhere external to the storage device's compartments onto which they are configured to illuminate, including being integrated into the ceiling of a That which is claimed:

1. A light projector comprising:
a light source
positioned external to a drawer of a medication storage device; and a processor configured to:
direct the projection of light to illuminate a first medication storage compartment, wherein the first medication storage compartment is included in the drawer and is illuminated without illuminating a second medication storage compartment of the medication storage device; and
direct the projection of light to illuminate the second medication storage compartment, wherein the second medication storage compartment is illuminated without illuminating the first medication storage compartment,
wherein directing the projection of light comprises adjusting a direction of projection along at least one axis.

2. The light projector of claim 1, wherein the light projector is configured to direct the projection of light to illuminate the first or the second medication storage compartment based upon a determination as to how far the drawer is extended into an open position and wherein the light projector is configured to adjust a direction of the projection of light in response to the determination as to how far the drawer is extended to the open position.

3. The light projector of claim 1 further comprising at least one reflective surface that is configured to direct light projected onto the medication storage device.

4. The light projector of claim 3, wherein the at least one reflective surface is configured to be moved to adjust the direction of the projection of light.

5. The light projector of claim 1, wherein the light projector is included in the medication storage device.

6. The light projector of claim 1, wherein the second medication storage compartment is included in the drawer.

7. The light projector of claim 6, wherein the first medication storage compartment is adjacent to the second medication storage compartment.

8. The light projector of claim 1, wherein the light source is located remote from the medication storage device.

9. The light projector of claim 8, wherein the processor is configured to facilitate communications with a device processor included in the medication storage device.

10. The light projector of claim 1, wherein the light projector is configured to project light that highlights at least one storage compartment included in the medication storage device.

11. The light projector of claim 1, wherein the light projector is configured to project user-readable information on at least one storage compartment included in the medication storage device.

12. A method of projecting light onto a medication storage device, comprising:
directing, by a processor, the projection of light, using a light projector, to illuminate a first medication storage compartment included in a drawer of a medication storage device, the light projector positioned external to the drawer, wherein illuminating the first medication storage compartment occurs without illuminating a second medication storage compartment of the medication storage device; and
directing the projection of light, using the light projector, to illuminate the second medication storage compartment, wherein illuminating the second medication storage compartment occurs without illuminating the first medication storage compartment, wherein directing the projection of light comprises adjusting a direction of projection along at least one axis.

13. The method of claim 12 further comprising dynamically determining the location of the first or the second medication storage compartment prior to projecting the light to illuminate the first or the second medication storage compartment, and adjusting a direction of the projection of light in response to determining the location of the first or the second medication storage compartment.

14. The method of claim 13, wherein dynamically determining a location of the first or the second medication storage compartment includes determining how far the drawer is extended into an open position.

15. The method of claim 12, wherein projecting the light further comprises projecting the light onto at least one reflective surface that is configured to direct the light.

16. The method of claim 15 further comprising moving the at least one reflective surface to adjust the direction of the projection of light.

17. The method of claim 12, wherein the light projector is integrated in the medication storage device.

18. The method of claim 12, wherein the light projector is remote from the medication storage device.

19. The method of claim 12, wherein projecting the light to illuminate the first or the second medication storage compartment comprises highlighting the first or the second medication storage compartment.

20. The method of claim 12, wherein directing the projection of light to illuminate the first or the second medication storage compartment comprises directing the projection of user-readable information on the first or the second medication storage compartment.

21. A medication storage device comprising:
a drawer comprising:
a first medication storage compartment; and
a second medication storage compartment;
a light projector comprising a light source positioned external to the drawer, the light projector configured to:
direct the projection of light to illuminate the first medication storage compartment, wherein the first medication storage compartment is illuminated without illuminating the second medication storage compartment; and
direct the projection of the light to illuminate the second medication storage compartment, wherein the second medication storage compartment is illuminated without illuminating the first medication storage compartment
wherein directing the projection of light comprises adjusting a direction of projection along at least one axis.

22. The medication storage device of claim 21 further comprising a processor configured to control the light projector.

23. The medication storage device of claim 22, wherein the drawer further comprises a reflective surface motor, and the processor is further configured to control the reflective surface motor.

24. The medication storage device of claim 23, wherein the processor is further configured to control the reflective surface motor based on how far the drawer is extended into an open position.

\* \* \* \* \*